(12) United States Patent
Epp et al.

(10) Patent No.: US 8,496,655 B2
(45) Date of Patent: Jul. 30, 2013

(54) SYSTEM AND METHOD FOR RESECTING A VALVE

(75) Inventors: Myra Epp, Grand Rapids, MI (US); Christine Stewart, Minneapolis, MN (US); David Shicheng Li, Ann Arbor, MI (US); Brian Matty, New York, NY (US); Michael J. O'Donnell, Ann Arbor, MI (US)

(73) Assignee: Michael J. O'Donnell, Ann Arbor, MI (US)

( * ) Notice: Subject to any disclaimer, the term of this patent is extended or adjusted under 35 U.S.C. 154(b) by 664 days.

(21) Appl. No.: 12/755,361

(22) Filed: Apr. 6, 2010

(65) Prior Publication Data

US 2010/0268226 A1 Oct. 21, 2010

Related U.S. Application Data

(60) Provisional application No. 61/167,013, filed on Apr. 6, 2009, provisional application No. 61/267,804, filed on Dec. 8, 2009.

(51) Int. Cl.
*A61B 18/18* (2006.01)

(52) U.S. Cl.
USPC ............................................ 606/48; 606/45

(58) Field of Classification Search
USPC .................................................... 606/41–48
See application file for complete search history.

(56) References Cited

U.S. PATENT DOCUMENTS

| | | | |
|---|---|---|---|
| 4,493,321 A | 1/1985 | Leather | |
| 5,370,685 A | 12/1994 | Stevens | |
| 5,545,214 A | 8/1996 | Stevens | |
| 5,690,662 A | 11/1997 | Chiu | |
| 6,033,419 A | 3/2000 | Hamblin, Jr. | |
| 6,769,434 B2 | 8/2004 | Liddicoat | |
| 7,201,761 B2 | 4/2007 | Woolfson | |
| 7,208,000 B2 | 4/2007 | Love | |
| 7,377,916 B2 | 5/2008 | Rudko | |
| 7,537,592 B2 | 5/2009 | Rudko | |
| 7,544,206 B2 | 6/2009 | Cohn | |
| 7,604,650 B2 | 10/2009 | Bergheim | |
| 2003/0014103 A1* | 1/2003 | Inoue | 623/1.35 |
| 2004/0116951 A1 | 6/2004 | Rosengart | |
| 2004/0127935 A1* | 7/2004 | VanTassel et al. | 606/200 |
| 2005/0055088 A1 | 3/2005 | Liddicoat | |
| 2005/0075659 A1 | 4/2005 | Realyvasquez | |
| 2005/0131438 A1 | 6/2005 | Cohn | |
| 2006/0235286 A1* | 10/2006 | Stone et al. | 600/381 |
| 2007/0185513 A1* | 8/2007 | Woolfson et al. | 606/170 |
| 2008/0188880 A1* | 8/2008 | Fischer et al. | 606/170 |
| 2009/0164004 A1 | 6/2009 | Cohn | |

* cited by examiner

*Primary Examiner* — Linda Dvorak
*Assistant Examiner* — Amanda Scott
(74) *Attorney, Agent, or Firm* — Shay Glenn LLP

(57) ABSTRACT

A system and method for resecting a valve in a patient, in which the system includes: a proximal frame and a distal frame opposite the proximal frame, each frame including a plurality of interconnectable frame segments, in which the proximal and distal frames are separated by an adjustable distance and positionable on opposite sides of the valve; an electrode, adjacent to the valve on at least one of the proximal and distal frames, that electrosurgically resects valve tissue; a proximal chamber and a distal chamber coupled to the proximal and distal frames, respectively, that allow passage of fluid and captures at least a portion of resected valve tissue, in which each chamber selectively operates in one of a radially collapsed mode and a radially expanded mode; and a drive system that adjusts the distance between the proximal and distal frames.

18 Claims, 8 Drawing Sheets

SYSTEM AND METHOD FOR RESECTING A VALVE

CROSS-REFERENCE TO RELATED APPLICATIONS

This application claims the benefit of U.S. Provisional Applications Nos. 61/167,013 filed 6 Apr. 2009 and 61/267,804 filed 8 Dec. 2009, which are incorporated in their entirety by this reference.

TECHNICAL FIELD

This invention relates generally to the surgical field, and more specifically to an improved system and method for resecting a valve in the cardiac surgery field.

BACKGROUND

Aortic stenosis is an abnormal narrowing of the aortic valve in the heart resulting in decreased cardiac function, which often leads to a deteriorating quality of life for those afflicted by the condition. The most effective conventional treatment for aortic stenosis is aortic valve replacement (AVR) by open heart surgery, which involves removing the existing native aortic valve and implanting an artificial aortic valve, but only a fraction of patients with aortic stenosis are able to undergo this invasive procedure. A less invasive procedure for aortic valve replacement under development is percutaneous or transcatheter AVR (PAVR or TAVI), in which the replacement valve is delivered as part of a stent valve delivery system through a guiding catheter via the vascular system by a transfemoral or directly via a transapical approach. In percutaneous AVR, a balloon catheter expands to compress the existing native valve to the blood vessel wall prior to insertion of the replacement valve. However, this procedure introduces significant risks, including paravalvular leakage, device embolization, device failure, inadequate valve sizing, induced conduction defects requiring a permanent pacemaker, obstruction of the coronary ostia, distal emboli resulting in stroke and mitral valve injury. Such risks are often increased for certain patients who, for example, have native valves with hardened leaflet calcifications that interfere with the replacement valve stent structure.

Thus, there is a need in the cardiac surgery field to create a system and method for resecting a valve. This invention provides such an improved system and method for resecting a valve.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System for Resecting a Valve

Figure 1A:
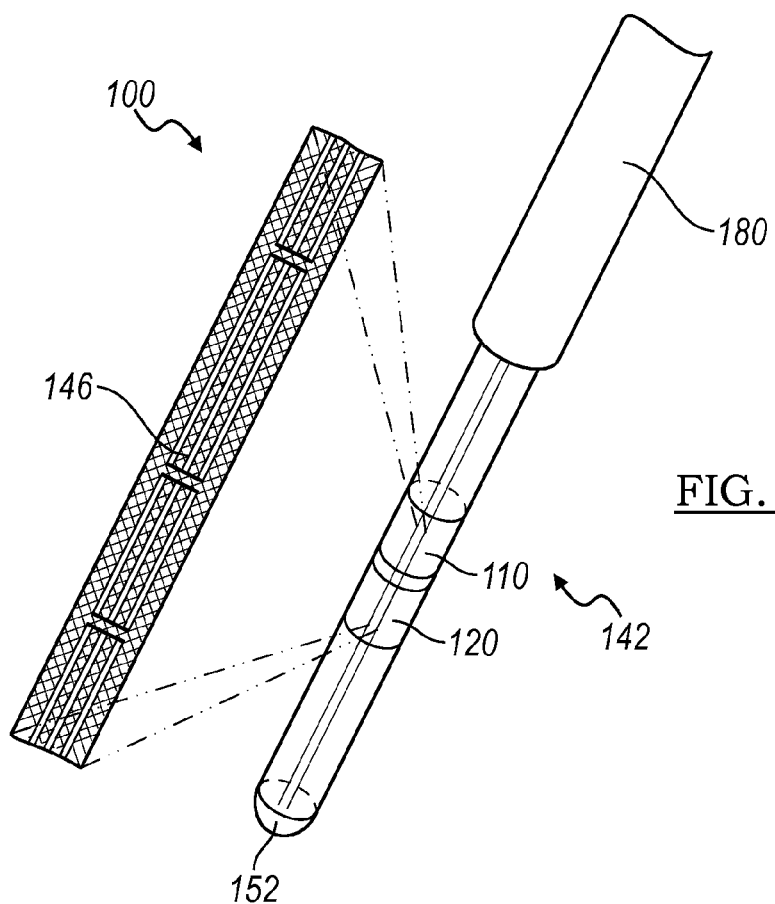
FIGS. 1A and 1B are partial views of the system of a preferred embodiment with the chambers and cutting frames in their collapsed and expanded modes, respectively.
Figure 1B:
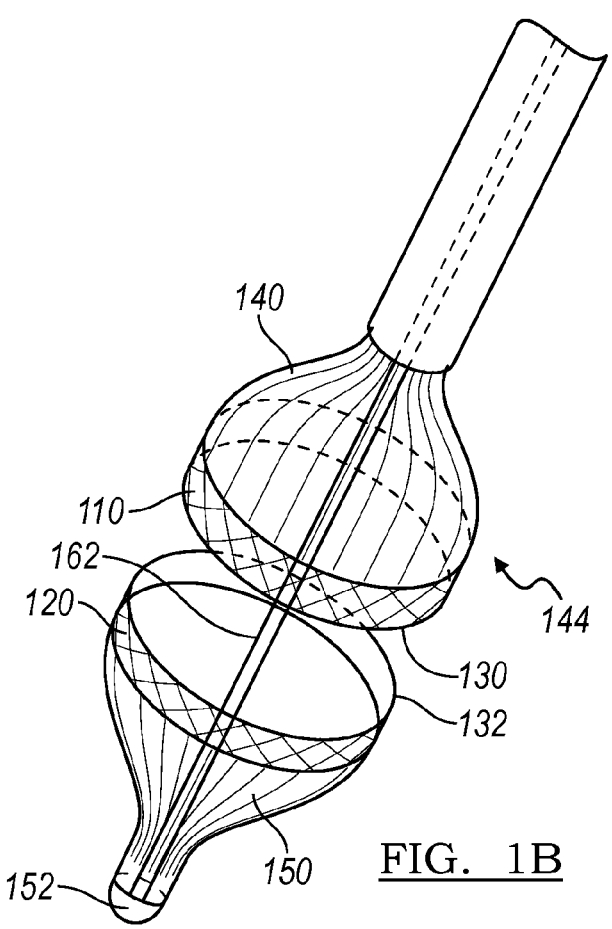
Figure 2A:
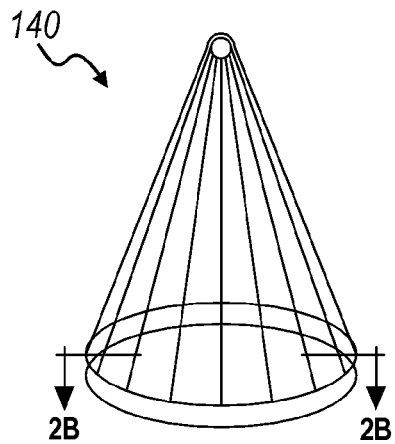
FIGS. 2A and 2B are perspective and cross-section views of the proximal and distal frames of the system of a preferred embodiment.
Figure 2A:
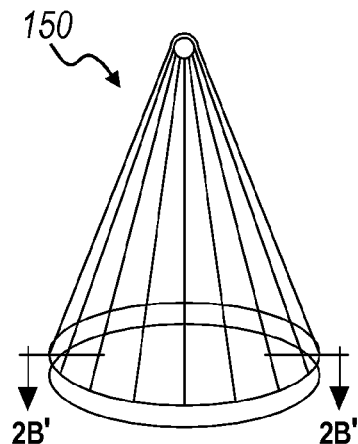
Figure 2B:
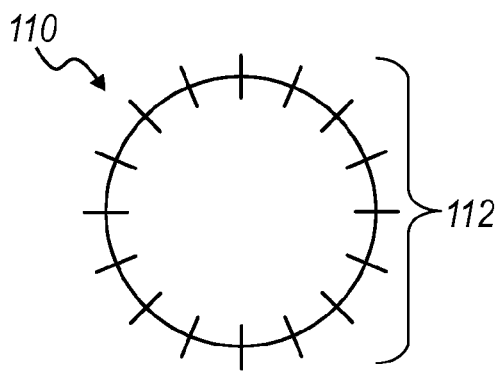
Figure 2B:
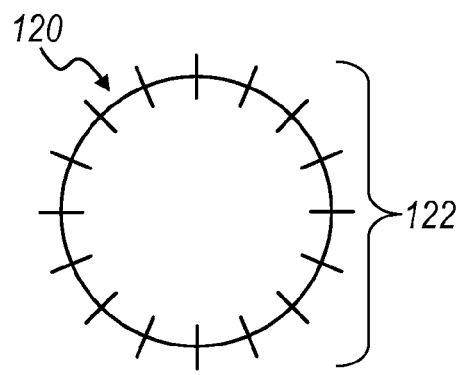
Figure 2C:
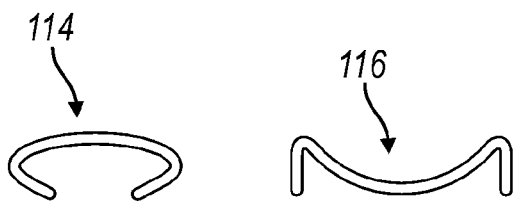
FIGS. 2C and 2D are detailed schematics of frame segments forming the proximal and distal frames of the system of a preferred embodiment.
Figure 2D:
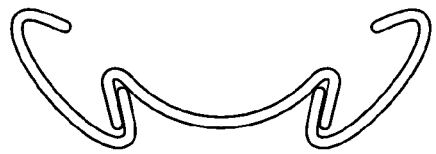

As shown in FIGS. 1 and 2, the system 100 of a preferred embodiment for resecting a valve in a patient preferably includes: a proximal frame 110 formed by a first plurality of interconnectable arc segments 112 and a distal frame 120 formed by a second plurality of interconnectable arc segments 122 opposite the proximal frame 110, in which the proximal and distal frames are separated by an adjustable distance 124 and positionable on opposite sides of the valve; at least one electrode on at least one of the proximal and distal frames that electrosurgically resects valve tissue; a proximal chamber 140 coupled to the proximal frame 110 and a distal chamber 150 coupled to the distal frame 120, in which the proximal and distal chambers allow passage of blood or other fluid and capture at least a portion of the resected valve tissue; and a control system 160 including a drive cable 162 that adjusts the distance 124 between the proximal and distal frames. Each of the proximal and distal chambers preferably operates in at least one of the following modes: a radially collapsed mode 142 in which the plurality of arc segments are nested, and a radially expanded mode 144, in which the plurality of arc segments are expanded relative to each other and interconnect to form a generally circular shape. The system 100 preferably further includes a delivery catheter 180 that delivers the proximal and distal frames and chambers to and from the valve, and the control system 160 preferably controls operation of the distal and proximal frames and distal and proximal chambers. The system 100 is preferably used to excise or resect the aortic valve of a human or other animal patient prior to aortic valve replacement, in particular percutaneous aortic valve replacement (PAVR). Preferably, the system removes all of the valve tissue and captures all of the removed valve tissue. However, in some embodiments, the system may remove only a portion of the valve tissue and/or capture only a portion of the valve tissue. For example, the system may be accompanied by another instrument that is operated to remove another portion of the valve tissue and/or capture another portion of the valve tissue, such that the system and the instrument (or multiple instruments) cooperate to completely excise and capture all of the valve tissue. In an alternative embodiment, the system is integrated with a system for aortic valve replacement in a single instrument, such as an instrument that incorporates a replacement valve with the system for minimally invasive electrosurgical valve excision. The system 100 may be used in a transfemoral approach, a transapical approach, or any other suitable approach to the aortic valve. The minimally invasive approach of the system to excise the valve complements the minimally invasive nature of percutaneous aortic valve replacement, and does not require the increased risk of cardiopulmonary bypass. However, the system may alternatively be used to excise any cardiac valve or other valve in the cardiovascular system, or any suitable tissue accessible by catheter. Entire excision of native valve tissue prior to valve replacement creates a known and consistent smooth annulus in which the replacement valve will be placed, which decreases or eliminates risks such as paravalvular leakage that are associated with a replacement valve needing to adapt to the native valve.

Figure 3A:
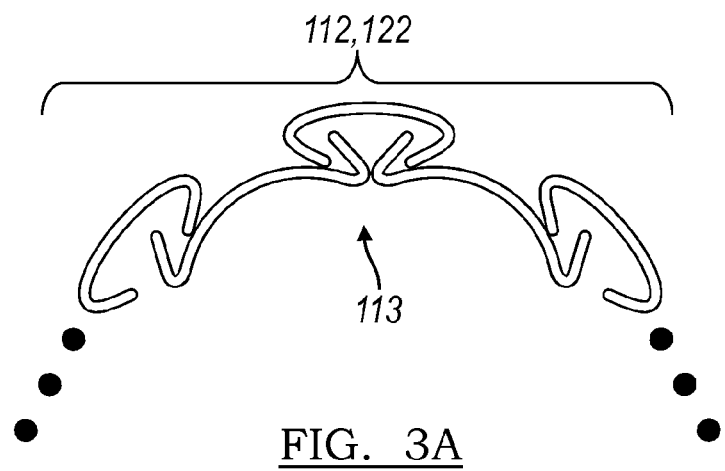
FIGS. 3A and 3B are partial schematics of the frame segments in the collapsed and expanded modes, respectively, of the chambers of the system of a preferred embodiment.
Figure 3B:
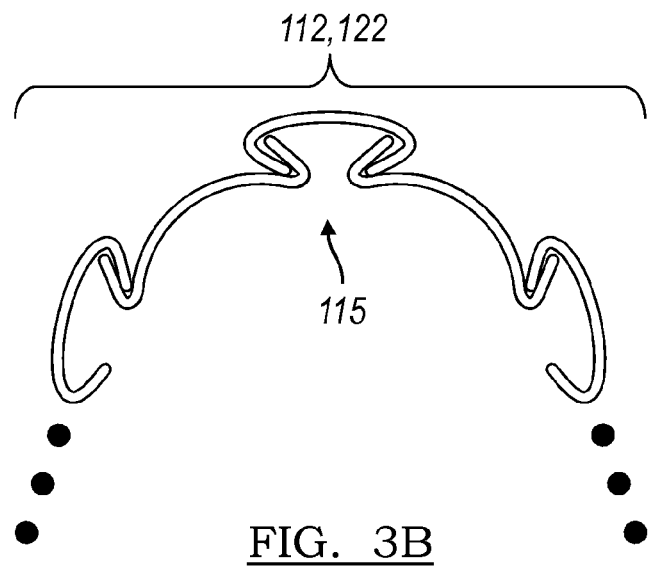
Figure 14:
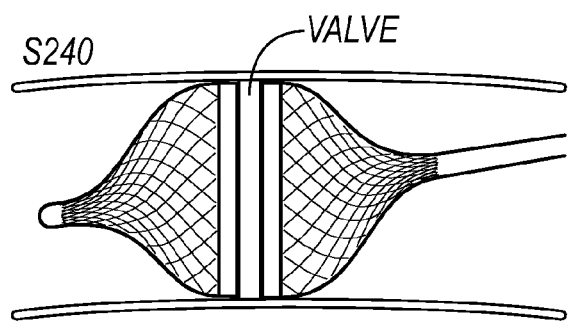
Figure 15:
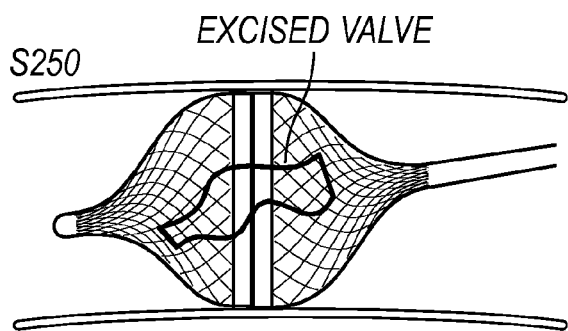
Figure 16A:
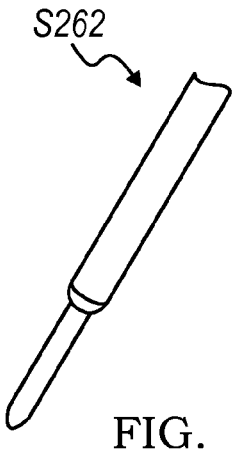
Figure 16B:
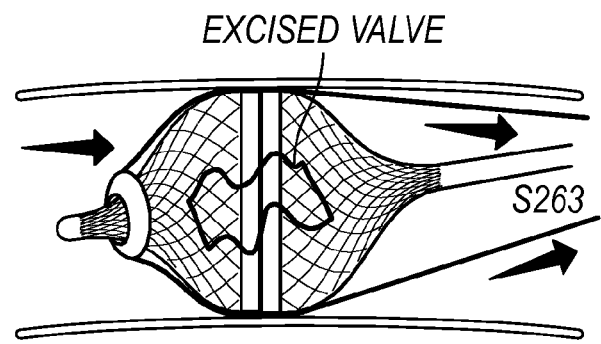
Figure 16C:
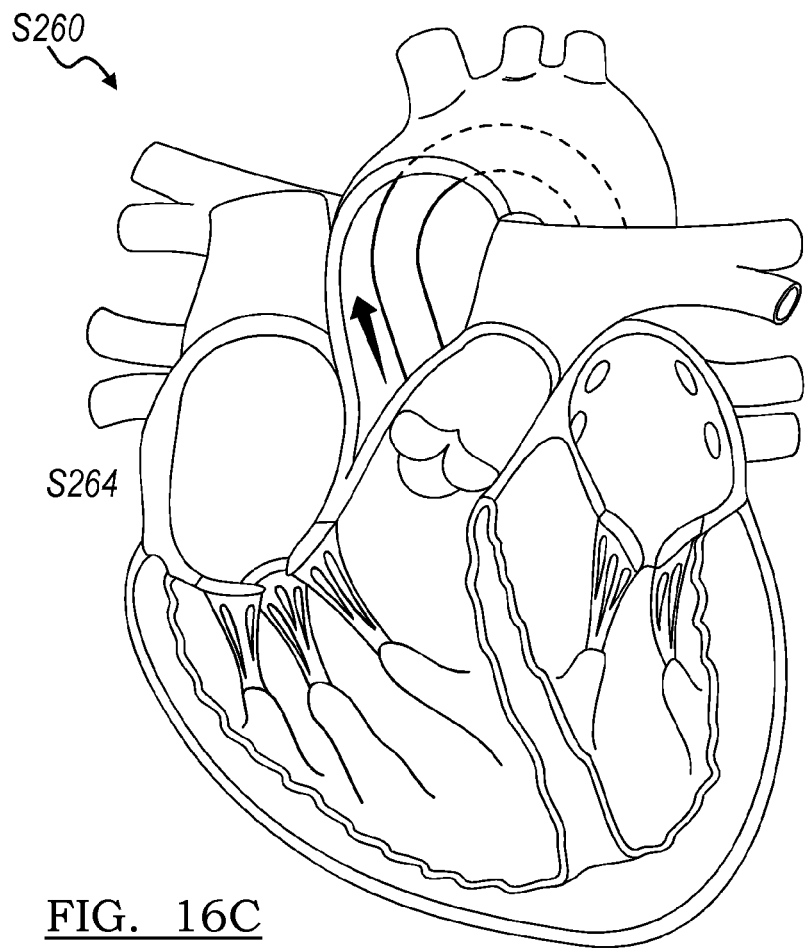

The proximal and distal frames 110 and 120, respectively, of the system function to provide structural support for the electrodes and the proximal and distal chambers. In some embodiments, the system may include only one frame, or may have three or more frames for any suitable number of electrodes and/or chambers. As shown in FIG. 14, the proximal and distal frames are preferably adjacent to one another, and face opposite to one another such that prior to excision of the valve, the valve tissue to be excised is positioned between the proximal and distal frames. When properly positioned in a transfemoral approach, the distal frame 120 is preferably located inferior to the aortic valve and the proximal frame 110 is preferably located superior to the aortic valve. Alternatively, when properly positioned in a transapical approach, the distal frame 120 is preferably located superior to the aortic valve and the proximal frame 110 is preferably located inferior to the aortic valve. As shown in FIGS. 3A and 3B, each frame preferably operates in at least two modes: a collapsed mode 113 and an expanded mode 115, which correspond to the collapsed and expanded modes 142 and 144, respectively, of the proximal and distal chambers. In the collapsed mode 113, the proximal or distal frame preferably radially collapses into a compact shape that can fit into the delivery catheter for positioning in and withdrawal from the patient, as well as pass through the opening of the native valve. In the expanded mode 115, the proximal or distal frame preferably radially expands to a full, substantially circular shape for valve tissue excision. The proximal and distal frames each preferably have a diameter of approximately 6 mm in the collapsed mode and approximately up to 26 mm in the expanded mode, but may alternatively be any suitable size and/or shape in either mode. For example, smaller dimensions may be appropriate for a pediatric patient. The proximal and distal frames preferably have a diameter ratio of approximately 1:4 in the collapsed mode relative to the expanded mode, but may alternatively have any suitable ratio. The proximal and distal frames are preferably identical in size, but may alternatively be different sizes and/or shapes.

As shown in FIGS. 2 and 3, each of the proximal and distal frames 110 and 120 includes a plurality of frame segments 112 and 122, respectively. The frame segments are preferably interconnecting arcuate pieces that form the frame structure. The frame segments are preferably approximate arc segments of a generally round ring. As shown in FIG. 3, each pair of adjacent arc segments preferably has complementary angled ends that unlock to enable the collapsed mode and lock to enable the expanded mode of the frame. More preferably, as shown in FIG. 2C, within a pair of adjacent frame segments in a plurality of frame segments, one arc segment preferably has ends 114 that are angled radially inwards, and the other adjacent arc segment preferably has ends 116 angled radially outwards, such that an inward angle end of one piece and an outward angle end of an adjacent piece engage to enable the expanded mode of the frame, and disengage to enable the collapsed mode of the frame. However, the frame segments may alternatively be any suitable length and shape, depending on the desired size and shape of the frame and/or interconnect in any suitable manner, such as with pins and slots. As an example, the frame segments may be shaped such that the frame in its expanded mode is elliptical or square. The number of frame segments that form the frame is a predetermined number, preferably based on the desired frame size that is dependent on the geometry of the intended replacement valve. In its expanded mode, the proximal frame 110 and/or distal frame preferably has a size and shape similar to that of the replacement valve.

Figure 4:
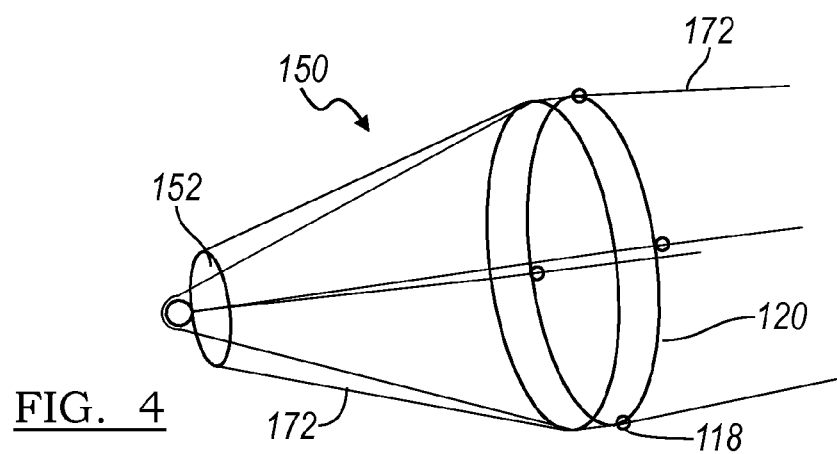
FIG. 4 is a side view of the distal chamber of the system of a preferred embodiment.

As shown in FIG. 4, the proximal and/or distal frame preferably includes at least one eyelet 118, such that a plurality of eyelets 118 is distributed around at least one of the frames. The eyelets 118 function to provide guidance for control wires that control a compression ring 152 on the distal chamber 150. As further described below, the compression ring 152 helps the distal frame 120 and distal chamber 150 transform from the expanded mode into the collapsed mode, and/or transform from the collapsed mode to the expanded mode. In a preferred embodiment, at least one of the proximal and distal frame preferably includes four eyelets equally distributed around the circumference of the frame at 90 degrees from each other when the frame is in its expanded mode, but may alternatively include any suitable number of eyelets arranged in any suitable arrangement. Alternatively, the proximal and/or distal frame may include channels, hooks, or any suitable guidance for the compression ring control wires.

The electrodes of the system function to cut through valve tissue. The system preferably includes at least one proximal electrode 130 on the proximal frame 110 and at least one distal electrode 132 on the distal frame, preferably on the frame segments around the perimeter of each frame, such that during valve excision, the valve tissue that is positioned between the opposing distal and proximal frames is approached by the electrodes from two sides, thereby reducing required cutting time. Alternatively, only one of the proximal and distal frames may include an electrode. The electrodes 130 and 132 preferably include electrode segments coupled to frame segments that collapse and expand correspondingly to the proximal and distal frames, although the specific geometry and arrangement of the electrodes may depend on the geometry of the frame segments and/or the anatomy of the valve tissue to be cut. The electrodes may, however, be of unitary construction such as being ring-shaped. The electrodes 130 and 132 preferably perform bipolar electrosurgery to cauterize and cut through the valve tissue, but may alternatively be any suitable kind of electrode capable of cutting through tissue. The electrodes are preferably powered with electrocautery current supplied by a bipolar electrosurgical generator, but the electrodes may additionally and/or alternatively be powered by any suitable radiofrequency or other suitable energy source. The electrodes are preferably similar to conventional bipolar electrosurgical electrodes, and are preferably made of a conductive material such as gold or silver to decrease the amount of time required to cut tissue. In an alternative embodiment, one of both of the frames may additionally and/or alternatively include other means for cutting through tissue, such as blades, lasers, or RF energy.

Figure 13A:
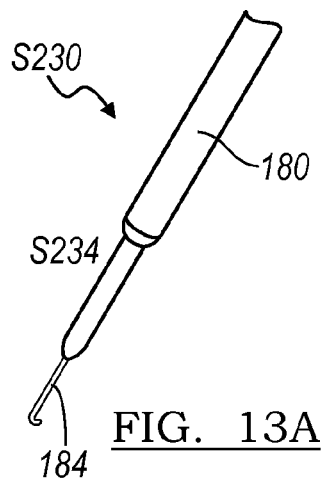
Figure 13B:
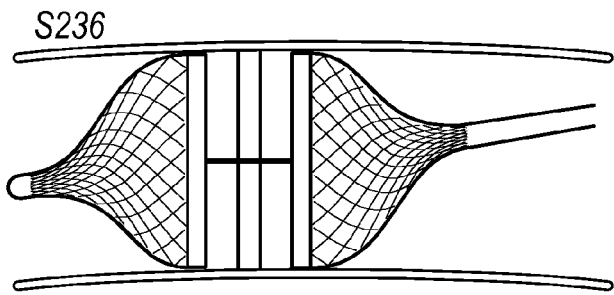
Figure 13C:
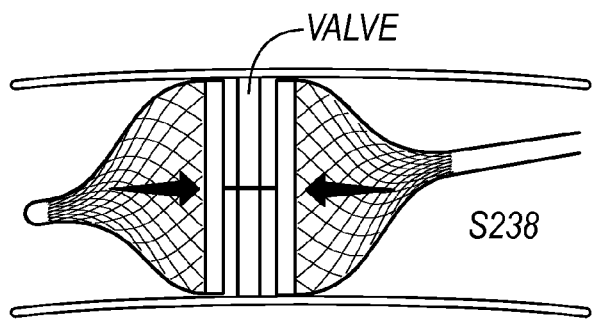

The proximal and distal chambers 140 and 150 of the system function to contain the valve tissue after valve excision. The proximal chamber 140 is preferably coupled to the proximal frame 110, and the distal chamber 150 is preferably coupled to the distal frame 120, although the system may alternatively include more or fewer chambers. As shown in FIG. 13, the proximal and distal chambers 140 and 150 are preferably opposed to one another on opposite sides of the native valve before valve excision, with open ends that face each other across the native valve. After the valve tissue is cut, the proximal chamber and/or distal chamber captures the excised or resected valve tissue. Similar to the proximal and distal frames, each chamber preferably operates in at least one of two modes: a collapsed mode 142 to fit within the delivery catheter and through the native valve before valve excision, and an expanded mode 144 to facilitate capture of the excised or resected valve tissue. The collapsed and expanded modes 142 and 144 of the chambers preferably correspond to the collapsed and expanded modes 113 and 115 of the frames, respectively, in that the frames and chambers are preferably in their collapsed modes simultaneously and in their expanded modes simultaneously. In the collapsed mode, each chamber preferably includes an interior space large enough to accommodate valve tissue, for containing the valve tissue during withdrawal from the patient through the delivery catheter. The proximal and distal chambers may be identical in size, such that their facing open ends are equal in size in the expanded mode, or one chamber may be slightly smaller than the other such that the open end of the smaller chamber nestles slightly within the open end of the larger chamber. Each of the proximal and distal chambers preferably includes a plurality of frame arms and a mesh filter.

Figure 5:
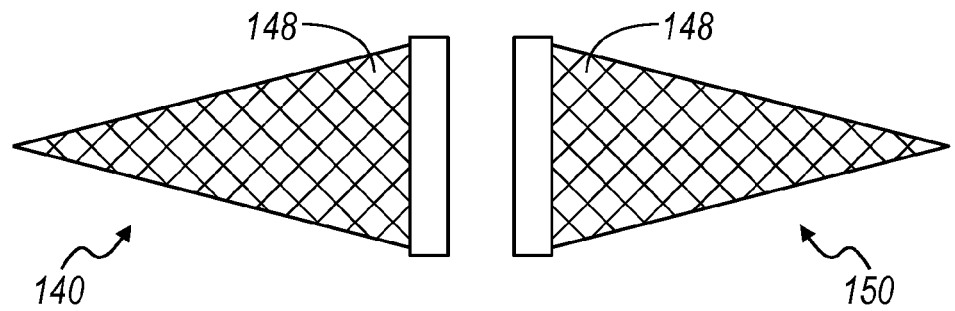
FIG. 5 is a side view of the proximal and distal chambers of the system of a preferred embodiment.

The plurality of frame arms 146 preferably provide structural support for the chamber, and deploy the chamber and frame into the expanded mode. In the collapsed mode of the chamber, the frame arms preferably collapse radially inwards, and in the expanded mode of the chamber, the frame arms preferably expand radially outwards. As shown in FIGS. 4 and 5, in the expanded mode of the chamber, the frame arms preferably define a generally conical shape, but may alternatively define a frustoconical shape, a bell shape (shown in FIG. 1), a cylinder, or any suitable shape. The plurality of frame arms 146 preferably self-expand, similar to conventional nitinol stents. However, the frame arms 146 may additionally and/or alternatively expand through actuated means such as balloon inflation, or any suitable mechanism. The frame arms 146 are preferably made of nitinol, similar to conventional stents, but may be made of another shape memory alloy or any suitable biocompatible material. The frame arms are preferably made in a manufacturing process similar to that of stents, such as laser cutting. The frame arms of the proximal chamber are preferably identical to those of the distal chamber, but the frame arms of the distal and proximal chambers may alternatively be different. In alternative embodiments, the proximal and/or distal chamber may lack a plurality of frame arms, such that the mesh filter is structural supported by only the proximal and/or distal frame around its perimeter, and/or another suitable attachment point.

Figure 6:
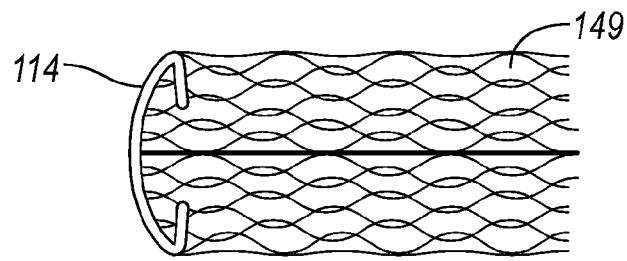
FIG. 6 is a partial side view of a frame segment and mesh segment of the system of a preferred embodiment.
Figure 7:
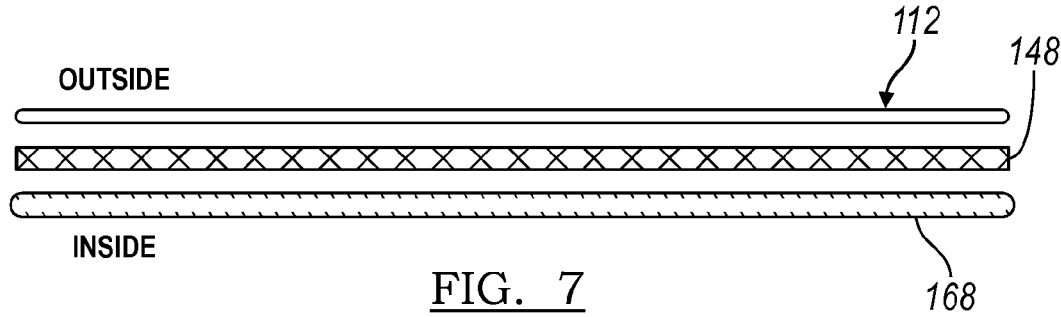
FIG. 7 is a cross-section schematic of a frame segment of the system of a preferred embodiment.

The mesh filter 148 preferably allows passage of fluid and captures the excised valve tissue after valve excision. The mesh filter 148 may capture other particles, such as calcium or other mineral deposits on the tissue and/or separated from the tissue. In some embodiments, the mesh filter 148 may include a single net-like piece that is coupled to some or all of the frame segments. In other embodiments, the mesh filter may include multiple overlapping mesh segments 149, such that each mesh segment is coupled to a frame segment (shown in FIG. 6) and overlaps with adjacent mesh segments a sufficient amount as to avoid gaps between mesh segments. As shown in FIG. 7, the mesh filter 148 is preferably attached to the inside surfaces of the frame arms 146 of the chamber, thereby substantially forming the walls of the chamber. Alternatively, the mesh filter 148 may be attached to the exterior surfaces of the frame arms 146 of the chamber, or any other suitable surface. The mesh filter 148 is preferably a mesh membrane with a mesh size of approximately 55 microns, but may have any suitable size mesh to allow blood to pass through the mesh filter, while preventing passage of and capturing excised valve tissue particles. The mesh membrane is preferably made of polyethylene, but may alternatively be made of any flexible mesh capable of being easily compacted in the collapsed state of the chamber. In alternative embodiments, the chamber may additionally and/or alternatively include other means to contain and/or excise the valve tissue from the area following valve excision, such as suction.

The distal chamber 150 preferably further includes a compression ring 152 that helps the distal chamber and distal frame transform from their expanded modes into their collapsed modes. The compression ring 152 preferably slidingly engages with the frame arms 146 of the distal chamber 150 to transition the distal chamber 150 from the expanded mode 142 to the collapsed mode 144. The compression ring 152 preferably includes a single central hole or lumen that slides over the exterior of the distal chamber 150, but the compression ring may alternatively include multiple holes or lumens. For example, in an embodiment in which the distal chamber 150 includes longitudinal frame arms that expand like an umbrella, the compression ring may have a compactly arranged plurality of holes (such as in a circle), in which each hole is slidingly engaged with a frame arm such that when the compression ring is drawn over the distal chamber, the frame arms are constrained to collapse relative to one another. As shown in FIG. 4, the compression ring is preferably drawn from the distal end of the distal chamber towards the proximal end of the distal chamber by at least one compression ring control wire 172. When the compression ring control wires 172 are pulled, the compression ring slides over the distal chamber in a proximal direction to help transform the distal chamber and distal frame from their expanded modes into their collapsed modes, particularly after valve excision. The compression ring may additionally and/or alternatively slide over the distal chamber in a distal direction to help transform the distal chamber and distal frame from their collapsed mode to their expanded modes. The compression ring control wires 172 are approximately equally distributed around the perimeter of the distal frame and distal chamber, guided through eyelets 118 on the distal frame and/or proximal frame 110 towards the compression ring. The system preferably includes four compression ring control wires, but may alternatively include any suitable number of compression ring control wires 172. Alternatively, the distal chamber may transition to the collapsed mode with any suitable mechanism or manner. When the distal chamber transitions to the collapsed mode, the proximal chamber preferably correspondingly returns to its collapsed mode as the proximal chamber is withdrawn, proximal pointed end first, back into the delivery catheter 180 after excision of the valve tissue, but the proximal chamber may additionally and/or alternatively include a compression ring or another similar structure to help return to its collapsed mode.

In a preferred embodiment, the system further includes a delivery catheter 180 that delivers the proximal and distal frames and chambers to the valve. The delivery catheter 180 is preferably similar to PAVR delivery catheters and other catheters that access the aortic valve, such as that described in U.S. Pat. No. 4,777,951 entitled, "Procedure and catheter instrument for treating patients with aortic stenosis", which is incorporated in its entirety by this reference. The delivery catheter 180 preferably accesses the vascular system by entering through a femoral artery, but may alternatively access the vascular system through any suitable artery, vein or other point of entry. Once within the aortic arch, the delivery catheter is preferably advanced until the collapsed distal chamber and distal frame pass through the aortic valve, and the aortic valve is properly positioned between the distal frame and the proximal frame 110 for valve excision. The delivery catheter preferably enables a second catheter to simultaneously access the aortic valve. This simultaneous access to the aortic valve allows, for example, a PAVR catheter to enter the vascular system through the second, unused femoral artery of the patient so that valve replacement may be performed very soon after native valve excision is completed, shortening the total surgery time and possibly reducing complications.

Figures 9, 10:
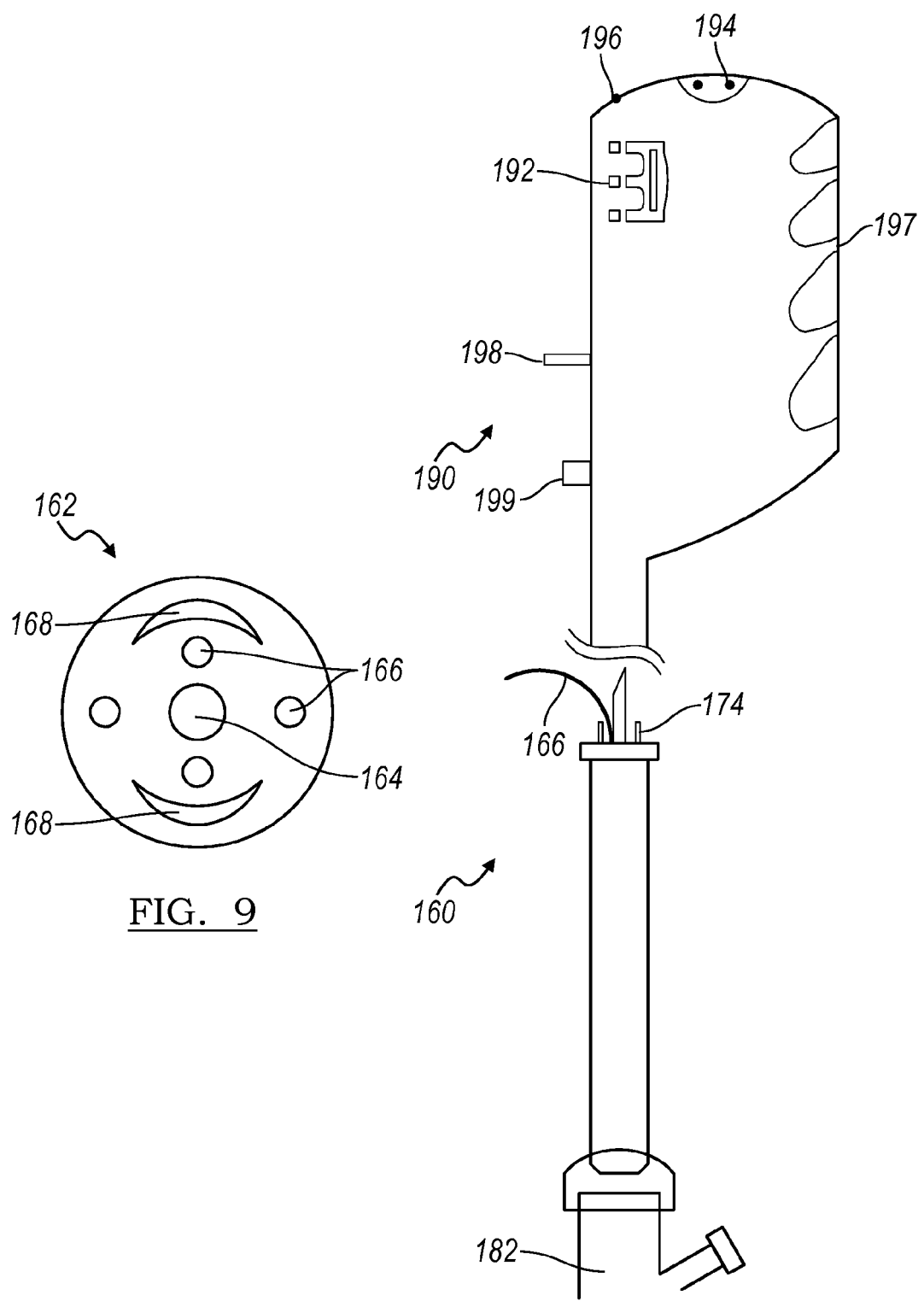
FIG. 9 is a cross-section schematic of the drive cable of the system of a preferred embodiment.
FIG. 10 is a side partial view of the power unit and delivery catheter of the system of a preferred embodiment.

As shown in FIG. 10, the proximal portion of the delivery catheter 180 preferably includes a hemostatic valve 182 such as a Tuohy-Borst hemostatic valve, which are commonly used in percutaneous procedures to provide a fluid seal that prevents "back-bleeding", or blood leakage or loss through the catheter. The proximal end of the delivery catheter may additionally and/or alternatively include any suitable mechanism to prevent blood leakage, such as a gasket or plug.

The control system 160 controls the operation of the distal and proximal frames and chambers, such as adjusting the distance 124 between the proximal and distal frames. The control system 160 preferably includes a drive system with a drive cable 162 that moves the distal and proximal frames relative to one another, a central guidewire 184 that provides control of the delivery catheter, the set of compression ring control wires 172 that move the compression ring 152, a set of current supply cables 174 that provide current to the electrodes, and a power unit 190 that supplies power to the system and provides an operation interface for the control system. The control unit is preferably handheld by a user outside the body of the patient, and may have finger grooves 197 and/or other contours to promote an ergonomic feel.

Figure 8:
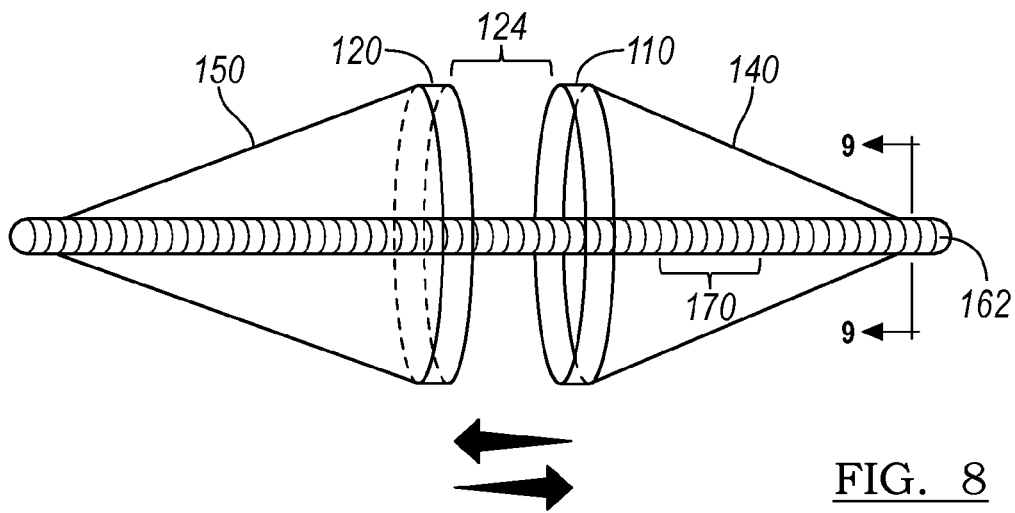
FIG. 8 is a schematic of the drive cable mechanism of the system of a preferred embodiment.

The drive cable 162 of the drive system functions to move the distal and proximal frames relative to one another. The drive cable 162 preferably selectively opens and closes the gap distance 124 between distal and proximal frames in which the native valve lies prior to valve excision. The drive cable preferably includes external threads 170 and runs coaxially inside the delivery catheter 180 and, as shown in FIG. 8, is preferably coaxial with the proximal chamber 140, the proximal frame 110, the distal frame 120, and the distal chamber 150. In one variation, the distal chamber 150 is fixed to the drive cable 162 and the proximal chamber 140 is held stationary and not fixed to the drive cable 162, such that rotation of the drive cable 162 rotates the distal chamber 150 and moves the distal chamber towards and away from the proximal chamber, thereby opening or closing the gap 124 between the distal and proximal frames (depending on the direction of rotation). Alternatively, the distal chamber may be held stationary and the proximal chamber may be fixed to the drive cable. In a second variation, the exterior of the drive cable and either the proximal chamber or distal chamber include reverse (left-hand) threads, such that rotation of the drive cable causes the distal and proximal frames to move toward and away from one another, similar to a turnbuckle. However, the drive system may additionally and/or alternatively include magnets and/or any suitable mechanism located in any suitable location to move the distal and proximal frames relative to one another.

The drive cable 162 of the drive system preferably includes a plurality of lumens that contain and guide the central guidewire, the compression ring control wires, and the current supply cables within the drive cable. As shown in FIG. 9, the drive cable preferably includes a central lumen 164 located at the center of the drive cable to accommodate the central guidewire 184, four approximately equally distributed lumens 166 for the compression ring control wires 172, and a two crescent-shaped lumens for the current supply cables 168. The drive cable 162 may additionally and/or alternatively include any suitable number, shape, and size of lumens that accommodate any suitable wires or objects that pass from the power unit to the distal end of the distal chamber. The central portion of the drive cable that includes the lumens may be independent of the exterior thread portion, such that as the drive cable rotates, the central portion of the drive cable does not rotate, thereby preventing the wires and cables passing through the lumens from twisting with the rotation. As an example, the central portion of the drive cable may be a rod that spins freely within an externally-threaded tube, aided by lubricants or a suitable mechanism.

Figure 12:
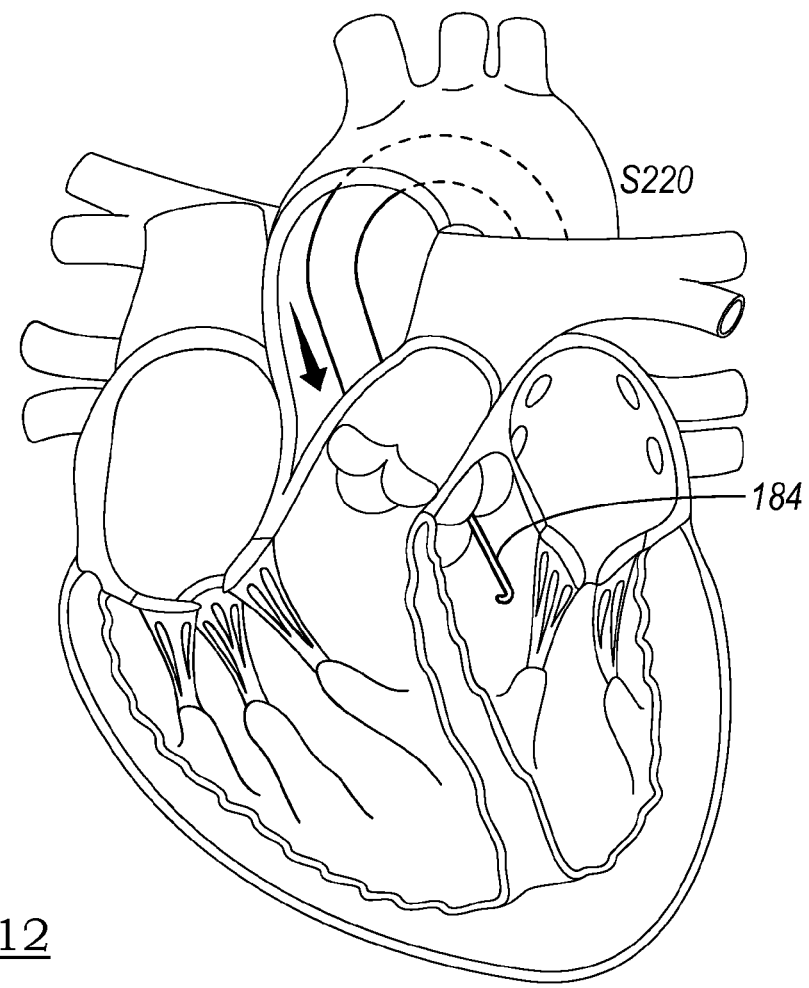

As shown in FIGS. 12 and 13, the central guidewire 184 of the control system functions to provide control of the delivery catheter and guide the delivery catheter through the vascular system to the valve. The central guidewire 184 is preferably similar to those known to one skilled in the art, such as the guidewire described in U.S. Pat. No. 4,777,951 referenced above, but may be any suitable kind of guidewire. As shown in FIG. 9, the central guidewire preferably pass axially within a central lumen of the drive cable, from the power unit to the distal end of the distal chamber.

As described above, the compression ring control wires 172 of the control system function to move the compression ring that transitions the distal frame 120 and chamber from the expanded mode to the collapsed mode. As shown in FIG. 9, the compression ring control wires preferably pass through a plurality of lumens 166 in the drive cable. As shown in FIG. 5, the compression ring control wires 172 preferably pass axially within designated lumens of the drive cable, from the power unit 190 to the compression ring. Near the power unit end, the compression ring control wires 172 may be braided into a single control cable and coupled to a control cable lever 198 traveling within a groove on the power unit 190. Pulling the lever proximally preferably retracts the set of compression ring control wires, thereby sliding the compression ring over the distal chamber to collapse the distal chamber. However, the compression ring control wires may alternatively be selectively pulled in any suitable manner, such as with a mechanism involving springs, notches, or catches. The compression ring control wires are preferably made of stainless steel, but may alternatively be made of any high tensile, biocompatible material or suitable material. The control wires may be operated on a pulley system, another continuous loop mechanism, or other suitable bidirectional control mechanism, such that pulling the compression ring control wires 172 in one direction compresses or retracts the distal chamber and pulling the compression ring control wires 172 in an opposite direction re-expands the distal chamber, thereby enabling transformation between the collapsed and expanded modes. A similar setup with another compression ring and control wires may additionally and/or alternatively be coupled to the proximal chamber to transform the proximal chamber from the expanded mode to the collapsed mode and/or from the collapsed mode to the expanded mode.

The current supply cables 174 of the control system function to supply current to the electrodes 130 and 132 that are used to excise the native valve tissue. The current supply cables 174 preferably supply bipolar electrocautery current or other suitable energy source to the proximal and/or distal frames. As shown in FIG. 9, the current supply cables preferably pass axially within designated lumens of the drive cable, from the power unit to the inner edges of the distal and proximal frames as shown in FIG. 7. The control subsystem preferably includes at least two current supply cables, one serving as an active path and one serving as a return path for the current. The control subsystem may, however, include any suitable number of current supply cables, such as a pair of current supply cables for each separate frame. The current supply cables 174 are preferably insulated with plastic or any suitable insulation, to help prevent unintentional electrical conduction between the current supply cables and portions of the drive cable, including other wires and cables passing through lumens within the drive cable 162.

Figure 11:
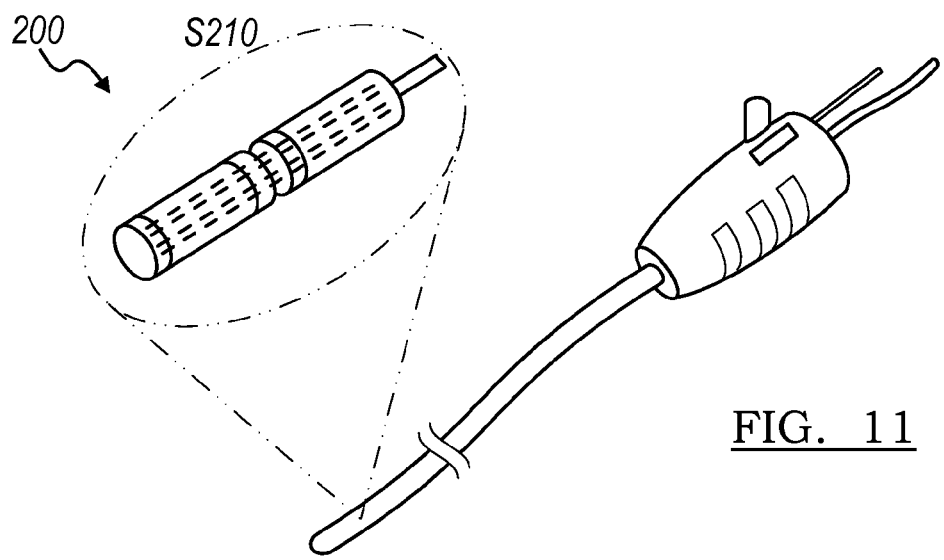
FIGS. 11-16 are schematics of the steps of the method of a preferred embodiment.

The power unit 190 of the control system functions to supply to the system and provides an operation interface for the control system. As shown in FIG. 11, the power unit preferably includes a drive unit 192 to control the drive cable, a coupling port 194 to connect to an electrocautery power supply, and a guidewire lumen port 196 that facilitates an "over the wire" delivery catheter insertion approach, a control cable lever 198, and a power switch 199 that turns the system on and off.

The drive unit 192 for controlling the drive cable 162 preferably includes controls such as a knob, switch, or lever that manipulates the drive cable in forward and reverse directions, and in a neutral operation. The drive unit 192 may include a motor, gears, pulleys, and/or any suitable drive control system. The drive unit is preferably battery-operated, but may additionally and/or alternatively be connected to an external power source. The drive unit 192 preferably operates with selected specified revolutions per minute (RPM), resulting in selected speeds at which the distal frame 120 and proximal frame move towards or away from one another. The drive unit may alternatively be external to the power unit, and connected to the drive cable with any suitable drivetrain system.

The coupling port 194 preferably includes contacts that connect to an external generator that generates electrocautery current, preferably bipolar electrocautery current. The specific frequency of current that the coupling port is preferably in the radiofrequency band, but may alternatively be any suitable frequency depending on the specific application.

The guidewire lumen port 196 preferably extends through the entire length of the power unit. As is known to one skilled in the art, in an "over the wire" delivery catheter insertion approach, the guidewire 184 is preferably inserted through the guidewire lumen and into the vascular system. The delivery catheter 180 is then inserted into the vascular system like a sleeve over the guidewire 184, following the trajectory of the guidewire in the vascular system.

The control cable lever 198, as mentioned above, provides selective manipulation of the compression ring control cables 172. The control cable lever 198 preferably moves within a groove on the power unit, and preferably provides tactile feedback such as a catch or latch that signals full retraction of the compression ring control cables, which indicates successful collapse of the distal chamber and distal frame 120. The feedback may alternatively and/or additionally include visual feedback (such as a light) and/or audio feedback (such as a click) that indicates the distal chamber and distal frame 120 are in their collapsed modes. The control cable lever 198 may include a similar feedback to indicate that the distal chamber and distal frame 120 are in their expanded modes. The control cable lever 198 may alternatively and/or additionally include any suitable mechanism, such as a slide switch, knob and or safety lock system.

2. Method of Resecting a Valve in a Patient

As shown in FIGS. 11-16, the method 200 of resecting a valve in a patient preferably includes the steps of: S210, which includes providing a system including a proximal frame and a distal frame opposing the proximal frame, wherein each of the proximal and distal frames includes a plurality of interconnectable frame segments, an electrode on the proximal and/or distal frame that is adapted to electrosurgially resect valve tissue, and a proximal chamber and distal chamber coupled to the proximal and distal frames, respectively, that are selectively operable in a radially collapsed mode and a radially expanded mode; S220, which includes navigating a delivery catheter through the vascular system of the patient, in which the proximal and distal chambers are in the collapsed mode and sheathed within the delivery catheter; S230, which includes positioning the proximal and distal frames on opposite sides of the valve; S40, which includes activating the electrode to resect the valve tissue; S50, which includes capturing the resected valve tissue in the proximal and/or distal chambers; and S260, which includes withdrawing the delivery catheter and resected valve tissue from the vascular system of the patient. The method is preferably used to excise the aortic valve of an animal (including a human), but may alternatively be used to excise any cardiac valve or other valve in the cardiovascular system, or any suitable tissue accessible by catheter. The method may be used in conjunction with a percutaneous artificial valve replacement procedure.

Step S210, which includes the step of providing a system having proximal and distal frames, an electrode, and proximal and distal chambers, preferably includes providing the system for resecting a valve described above in Section 1, but may alternatively include providing elements of another suitable system deliverable by catheter. For example, instead of including an electrode for electrosurgical removal of the valve, the system may include a cutting blade that cuts through valve tissue.

Step S220, which includes the step of navigating a delivery catheter through the vascular system of a patient, preferably includes the steps of: introducing a central guidewire into the vascular system, navigating the central guidewire to the native valve, and introducing the delivery catheter and system over the guidewire. During step S220, the proximal and distal chambers are in the collapsed mode and sheathed within the delivery catheter. The central guidewire preferably is introduced into the vascular system by entering a femoral artery in a transfemoral approach, and navigated superiorly through the aorta, around the aortic arch, and towards the aortic valve. However, the central guidewire may alternatively be introduced into the vascular system through direct entry of the left ventricle of the heart in a transapical approach, or any suitable approach. The delivery catheter and system preferably are slipped over the guidewire and follow the path defined by the guidewire towards the aortic valve. The step of inserting the system into the vascular system of the patient is preferably similar that used in percutaneous aortic valve replacement. However, the guidewire, delivery catheter, and system may alternatively be inserted into the vascular system of the patient through any suitable process.

S230, which includes positioning the proximal and distal frames on opposite sides of the valve, preferably includes the steps of: passing the delivery catheter through the native valve until the distal frame is on the far side of the native valve, unsheathing the distal chamber and distal frame from the delivery catheter S234, allowing the distal chamber, distal frame, proximal chamber, and proximal frame to transform into their expanded modes S236, and actuating the proximal and distal frames towards each other such that the electrode is adjacent to the valve S238. The step S230 of positioning the proximal and distal frames on opposite sides of the valve preferably approaches the valve from one direction. Actuating the proximal and distal frames S238 preferably involves closing a gap defined by the proximal and distal frames in which the valve lies, which is preferably performed by turning an externally threaded drive cable coupled to the proximal and distal chambers. The gap may be a preset separation distance between the proximal and distal frames, such as a gap distance established during manufacturing and/or a gap distance established prior to operation by a surgeon, or any suitable gap distance. In one variation, one of the proximal chamber and distal chamber is fixed to the drive cable and the other chamber is held stationary, such that rotation of the drive cable rotates the distal chamber and moves the distal chamber towards and away from the proximal chamber, thereby opening and closing the gap between the distal and proximal frames. In a second variation, the exterior of the drive cable and either the proximal chamber or distal chamber include reverse (left-hand) threads, such that rotation of the drive cable causes the distal and proximal frames to move toward and away from one another, similar to a turnbuckle. During the step of actuating the proximal and distal frames, the proximal and distal frames and chambers are preferably operated in their expanded modes.

S240, which includes activating the electrode to resect the valve tissue, preferably includes providing electrocautery current to the electrode. Both the proximal and distal frames preferably include an electrode on opposing faces adjacent to the valve, such that the valve tissue that is positioned between the opposing distal and proximal frames is approached by the electrodes from two sides, thereby reducing required cutting time. The step of providing electrocautery current preferably involves the use of an external bipolar electrocautery or radiofrequency power supply connected to the distal and proximal frames through insulated current supply wires passing within the delivery catheter. Providing bipolar electrocautery current preferably cuts and excises the valve using electrosurgery technology. In other embodiments, the valve may additionally and/or alternatively be removed with include any radiofrequency or suitable form of energy, or with blade or other suitable cutting means.

S250, which includes capturing the resected valve tissue in the proximal and/or distal chambers, preferably involves filtering the blood surrounding the site of the valve with the use of mesh in the distal and/or proximal chambers. The mesh preferably allows passage of blood and other fluid, but contains resected valve tissue and/or other particles larger than the mesh size.

S260, which includes withdrawing the delivery catheter and resected valve tissue from the vascular system of the patient, preferably includes the steps of: returning the proximal and distal chambers to the collapsed mode 5262, withdrawing the system into the delivery catheter, and removing the delivery catheter from the vascular system S264. The step S262 of returning the proximal and distal chambers to their collapsed modes preferably includes moving a compression ring 5263 slidingly engaged with the distal chamber to radially compress the distal chamber into the collapsed mode. The compression ring is preferably located on the distal end of the distal chamber, which selectively slidingly engages with the distal chamber when pulled in a proximal direction with control wires, thereby causing the distal chamber to collapse and contract. The step of returning the proximal chamber and proximal frame to the collapsed mode preferably includes retracting the proximal chamber into the delivery catheter apex-first. During the step S264 of removing the delivery catheter from the vascular system of the patient, the proximal and distal frames and chambers are preferably operated in their collapsed modes. The steps of withdrawing the system into the delivery catheter and removing the delivery catheter from the vascular system are preferably similar to that used in percutaneous aortic valve replacement.

As a person skilled in the art will recognize from the previous detailed description and from the figures and claims, modifications and changes can be made to the preferred embodiments of the invention without departing from the scope of this invention defined in the following claims.

We claim:

1. A system for resecting a valve in a patient, comprising:
a proximal ring comprising a first plurality of nesting and interconnectable frame segments and a distal ring comprising a second plurality of nesting and interconnectable frame segments that is opposite the proximal ring; wherein the proximal and distal rings are separated by an adjustable distance and positionable on opposite sides of the valve;
an electrode on the proximal ring and a second electrode on the distal ring configured to supply bipolar electrocautery current between the proximal ring and the distal ring that electrosurgically resects valve tissue;
a proximal chamber coupled to the proximal ring and a distal chamber coupled to the distal ring, wherein each of the proximal and distal chambers allows passage of fluid and captures at least a portion of the resected valve tissue, wherein each of the proximal and distal chambers selectively operates in one of the following modes:
a radially collapsed mode, wherein the plurality of frame segments are nested; and
a radially expanded mode, wherein the plurality of frame segments are expanded relative to each other and interconnect to form a generally circular shape,
wherein the proximal chamber and the distal chamber are configured to be collapsed with the proximal and distal rings together enclosing the resected valve tissue; and
a drive system that adjusts the distance between the proximal and distal rings.

2. The system of claim 1, wherein each of the first and second pluralities of frame segments has angled ends that complementarily mate with the angled ends of adjacent frame segments.

3. The system of claim 1, wherein at least one of the first and second pluralities of frame segments includes an arc segment having a radially inward angled end and another frame segment having a radially outward angled end that engages with the inward angled end in the expanded mode.

4. The system of claim 1, wherein each of the proximal and distal chambers includes a plurality of frame arms that collapse radially inwards in the collapsed mode, and open radially outwards in the expanded mode.

5. The system of claim 4, further comprising a compression ring that slidingly engages with the frame arms of the distal chamber to perform at least one of transitioning the distal chamber from the expanded mode to the collapsed mode and transitioning the distal chamber from the collapsed mode to the expanded mode.

6. The system of claim 5, wherein the compression ring is drawn from a distal end of the distal chamber towards a proximal end of the distal chamber along the frame arms of the distal chamber by a control wire.

7. The system of claim 6, wherein the control wire passes through an eyelet coupled to at least one of the distal and proximal rings.

8. The system of claim 1, wherein at least one of the proximal and distal chambers is conical.

9. The system of claim 1, wherein at least one of the proximal and distal chambers includes a mesh filter.

10. The system of claim 1, wherein the drive system includes a drive cable that is externally threaded.

11. The system of claim 10, wherein the drive cable includes both right-hand and left-hand threads.

12. The system of claim 10, wherein the drive cable is substantially coaxial with the proximal and distal chambers.

13. The system of claim 1, further comprising a compression ring that slidingly engages with the distal chamber to transition the distal chamber from the expanded mode to the collapsed mode.

14. A method for resecting a valve in a patient using a system having
- a proximal ring and a distal ring opposing the proximal ring, wherein each of the proximal and distal rings includes a plurality of nested and interconnectable frame segments;
- an electrode on the proximal ring and a second electrode on the distal ring, where the electrode and the second electrode are adapted to electrosurgically resect valve tissue between the proximal and distal rings; and
- a proximal chamber and distal chamber coupled to the proximal and distal rings, respectively, that are selectively operable in one of a radially collapsed mode in which the frame segments are nested and a radially expanded mode in which the frame segments are expanded relative to each other; the method comprising:
navigating a delivery catheter through the vascular system of the patient, wherein the proximal and distal chambers are in the collapsed mode and sheathed within the delivery catheter;
positioning the proximal and distal rings on opposite sides of the valve;
activating the electrodes to resect the valve tissue;
capturing the resected valve tissue in at least one of the proximal and distal chambers; and
withdrawing the delivery catheter and resected valve tissue from the vascular system of the patient.

15. The method of claim 14, wherein the step of positioning the proximal and distal rings includes unsheathing the system from the delivery catheter, operating the proximal and distal chambers in the expanded mode, and actuating the proximal and distal rings towards each other such that the electrodes are adjacent to the valve.

16. The method of claim 14, wherein the step of withdrawing the system from the vascular system of the patient includes returning the proximal and distal chambers to the collapsed mode.

17. The method of claim 16, wherein the step of returning the proximal and distal chambers to the collapsed mode includes moving a compression ring slidingly engaged with the distal chamber to radially compress the distal chamber into the collapsed mode.

18. A system for resecting a valve in a patient, comprising:
- a proximal ring including a first plurality of nesting frame segments and a distal ring including a second plurality of nesting frame segments that is opposite the proximal ring; wherein the proximal and distal rings are separated by an adjustable distance and positionable on opposite sides of the valve;
- an electrode on each of the proximal and distal rings that electrosurgically resects valve tissue;
- a proximal chamber coupled to the proximal ring and a distal chamber coupled to the distal ring, wherein each of the proximal and distal chambers includes a plurality of frame arms and a mesh filter that allows passage of fluid and is configured to retain at least a portion of resected valve tissue, wherein each of the proximal and distal chambers selectively operates in one of the following modes:
  - a radially collapsed mode, wherein the plurality of frame segments are nested and the plurality of frame arms are radially collapsed; and
  - a radially expanded mode, wherein the plurality of frame segments interconnect to form a generally circular shape and the plurality of frame arms are radially expanded; and
- a drive system including an actuated, externally threaded drive cable that adjusts the distance between the proximal and distal frames.

\* \* \* \* \*